US010639481B2

(12) United States Patent
Younker et al.

(10) Patent No.: US 10,639,481 B2
(45) Date of Patent: May 5, 2020

(54) POWER SOURCE LONGEVITY

(71) Applicant: Medtronic, Inc., Minneapolis, MN (US)

(72) Inventors: Gregory A. Younker, White Bear Township, MN (US); Karen J. Kleckner, Blaine, MN (US); Donald R. Merritt, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 249 days.

(21) Appl. No.: 15/864,380

(22) Filed: Jan. 8, 2018

(65) Prior Publication Data

US 2019/0209847 A1 Jul. 11, 2019

(51) Int. Cl.
*A61N 1/37* (2006.01)
*A61N 1/378* (2006.01)

(52) U.S. Cl.
CPC ............ *A61N 1/3708* (2013.01); *A61N 1/378* (2013.01)

(58) Field of Classification Search
CPC ......... A61N 1/37; A61N 1/3708; A61N 1/378
See application file for complete search history.

(56) References Cited

U.S. PATENT DOCUMENTS

| 4,259,639 A | 3/1981 | Renirie |
| 4,290,429 A | 9/1981 | Blaser |
| 4,448,197 A | 5/1984 | Nappholz et al. |
| 4,715,381 A | 12/1987 | Moberg |
| 5,031,616 A * | 7/1991 | Mann .................. A61N 1/36514 607/11 |
| 5,127,402 A * | 7/1992 | Mann .................. A61N 1/36514 607/11 |
| 5,370,668 A | 12/1994 | Shelton et al. |

(Continued)

FOREIGN PATENT DOCUMENTS

WO 2008042733 A2 4/2008

OTHER PUBLICATIONS (PCT/US2018/064953) PCT Notification of Transmittal of the International Search Report and the Written Opinion of the International Searching Authority, dated Feb. 27, 2019, 11 pages.

*Primary Examiner* — Christopher A Flory
(74) *Attorney, Agent, or Firm* — Shumaker & Sieffert, P.A.

(57) ABSTRACT

In some examples, determining an estimated remaining longevity of a power source of an implantable medical device comprises determining values of one or more parameters of the power source and one or more operational parameters of the implantable medical device; calculating, based on at least some of the determined parameter values, a first estimated duration until one of the determined parameters of the power source reaches a pre-recommended replacement time (pre-RRT) threshold and adding a timer duration to determine a first estimated longevity value; calculating, based on at least some of the determined parameter values, a second estimated duration until one of the determined parameters of the power source reaches a recommended replacement time (RRT) backup threshold as a second estimated longevity value; determining the estimated remaining longevity based on the two estimated longevity values; and indicating the determined estimated remaining longevity.

26 Claims, 11 Drawing Sheets

(56) References Cited

U.S. PATENT DOCUMENTS

| | | | |
|---|---|---|---|
| 5,391,193 A | 2/1995 | Thompson | |
| 5,402,070 A | 3/1995 | Shelton et al. | |
| 5,458,624 A | 10/1995 | Renirie et al. | |
| 5,620,474 A | 4/1997 | Koopman | |
| 5,713,936 A | 2/1998 | Staub et al. | |
| 5,741,307 A | 4/1998 | Kroll | |
| 5,769,873 A | 6/1998 | Zadeh | |
| 5,800,472 A | 9/1998 | Mann | |
| 6,108,579 A * | 8/2000 | Snell | A61N 1/3708 607/29 |
| 6,148,235 A | 11/2000 | Kuiper | |
| 6,154,675 A | 11/2000 | Juran et al. | |
| 6,167,309 A | 12/2000 | Lyden | |
| 6,185,461 B1 * | 2/2001 | Er | G16H 40/63 607/27 |
| 6,400,988 B1 | 6/2002 | Gurewitch | |
| 6,671,552 B2 | 12/2003 | Merritt et al. | |
| 6,760,625 B1 | 7/2004 | Kroll | |
| 6,885,894 B2 | 4/2005 | Stessman | |
| 6,901,293 B2 | 5/2005 | Rogers et al. | |
| 7,123,964 B2 | 10/2006 | Betzold et al. | |
| 7,191,005 B2 | 3/2007 | Stessman | |
| 7,542,801 B2 | 6/2009 | Rogers | |
| 7,711,426 B2 | 5/2010 | Armstrong et al. | |
| 7,848,812 B2 | 12/2010 | Crowley et al. | |
| 7,877,145 B2 | 1/2011 | Russie | |
| 7,941,220 B2 | 5/2011 | Tobacman | |
| 8,055,343 B2 | 11/2011 | Gandhi et al. | |
| 8,090,566 B2 | 1/2012 | Brown | |
| 8,131,367 B2 | 4/2012 | Rogers et al. | |
| 8,214,164 B2 | 7/2012 | Gandhi et al. | |
| 8,417,338 B2 | 4/2013 | Rogers et al. | |
| 8,452,395 B2 | 5/2013 | Crespi | |
| 8,612,167 B2 | 12/2013 | Schmidt et al. | |
| 8,639,338 B2 | 1/2014 | Rogers et al. | |
| 8,706,218 B2 | 4/2014 | Crespi | |
| 8,718,771 B2 | 5/2014 | Gandhi et al. | |
| 8,823,382 B2 | 9/2014 | Rondoni et al. | |
| 8,868,187 B2 | 10/2014 | Gandhi et al. | |
| 8,942,935 B2 | 1/2015 | Michaels et al. | |
| 8,996,113 B2 | 3/2015 | Ries et al. | |
| 9,616,238 B2 | 4/2017 | Demmer et al. | |
| 9,656,088 B2 | 5/2017 | Schilling et al. | |
| 2003/0065366 A1 | 4/2003 | Merritt et al. | |
| 2004/0039424 A1 | 2/2004 | Merritt et al. | |
| 2004/0199146 A1 | 10/2004 | Rogers et al. | |
| 2007/0150018 A1 | 6/2007 | Betzold et al. | |
| 2007/0179549 A1 * | 8/2007 | Russie | A61N 1/3708 607/29 |
| 2008/0097544 A1 | 4/2008 | Gandhi et al. | |
| 2009/0182517 A1 | 7/2009 | Gandhi et al. | |
| 2009/0312809 A1 | 12/2009 | Gandhi et al. | |
| 2011/0106213 A1 | 5/2011 | Davis et al. | |
| 2011/0208455 A1 | 8/2011 | Tobacman | |
| 2012/0101546 A1 | 4/2012 | Stadler et al. | |
| 2012/0109248 A1 | 5/2012 | Danielsson et al. | |
| 2012/0265266 A1 | 10/2012 | Colborn | |
| 2013/0231881 A1 | 9/2013 | Rogers et al. | |
| 2014/0277248 A1 | 9/2014 | Younker et al. | |
| 2015/0070022 A1 | 3/2015 | Gordon et al. | |
| 2015/0157866 A1 | 6/2015 | Demmer et al. | |
| 2016/0067510 A1 | 3/2016 | Norton et al. | |
| 2016/0151631 A1 | 6/2016 | Schilling et al. | |
| 2018/0372805 A1 * | 12/2018 | Fischer | G01R 31/392 |

* cited by examiner

POWER SOURCE LONGEVITY

TECHNICAL FIELD

The disclosure relates generally to medical systems and, more particularly, implantable medical devices having power sources.

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion, or defibrillation. In some cases, an implantable medical device may sense intrinsic depolarizations of the heart, and control the delivery of therapeutic stimulation to the heart based on the sensing. Some implantable medical devices provide cardiac sensing functionality without delivery of therapy. Some implantable medical devices are used to provide therapy and/or monitoring for any of a variety of conditions, including neurological or gastrological systems, as examples.

Cardiac resynchronization therapy (CRT) is one type of therapy delivered by an implantable medical device. Cardiac resynchronization therapy may help enhance cardiac output by resynchronizing the electromechanical activity of the ventricles of the heart. Ventricular desynchrony may occur in patients that suffer from congestive heart failure (CHF).

Implantable medical devices are typically powered by internal batteries, and battery depletion is inevitable. Many implantable medical devices are provided with the ability to communicate a "recommended replacement time" (RRT). The RRT informs the clinician that the device's power supply is nearing, but has not yet reached end-of-service (EOS), the point at which the power supply cannot provide sufficient energy to keep the device operable. The advance warning provided by an RRT gives the clinician the opportunity to take appropriate measures (e.g., to replace the device prior to EOS). Some implantable medical devices derive estimates of remaining battery life, which may include periodic measurements of battery voltage and either, or both of, battery impedance and current drain.

SUMMARY

In general, this disclosure is directed to systems and techniques for determining an estimated remaining longevity of a power source of an implantable medical device (IMD), such as a CRT device. The systems and techniques described herein may improve the useful life of the power source (e.g., the battery) of the IMD. The IMD may include processing circuitry configured to indicate power source events (e.g., a RRT for the power source or an EOS for the power source). The techniques may facilitate setting RRT later than is typical. For example, by setting the RRT in a plateau of the power source's characteristic depletion graph, as described further herein, the useful capacity of the power source may be improved over techniques that set RRT above the plateau.

In an example, a method for determining an estimated remaining longevity of a power source of an implantable medical device comprises: determining values of one or more parameters of the power source and one or more operational parameters of the implantable medical device; calculating, based on at least some of the determined parameter values, a first estimated duration until one of the determined parameters of the power source reaches a pre-recommended replacement time (pre-RRT) threshold and adding a timer duration to determine a first estimated longevity value; calculating, based on at least some of the determined parameter values, a second estimated duration until one of the determined parameters of the power source reaches a recommended replacement time (RRT) backup threshold as a second estimated longevity value; determining the estimated remaining longevity based on the two estimated longevity values; and indicating the determined estimated remaining longevity.

In an example, a medical device system for determining an estimated remaining longevity of a power source comprises: an implantable medical device (IMD) that comprises the power source; processing circuitry, configured to determine values for at least one parameter of the power source and at least one operational parameter of the IMD, wherein the processing circuitry is configured to calculate, based on one or more of the determined parameter values, a first estimated duration until the at least one parameter of the power source reaches a pre-recommended replacement time (pre-RRT) threshold, and the processing circuitry is configured to add a timer duration to determine a first estimated longevity value, wherein the processing circuitry is configured to calculate, based on the one or more of the determined parameter values, a second estimated duration until the at least one parameter of the power source reaches a recommended replacement time (RRT) backup threshold as a second estimated longevity value, and wherein the processing circuitry is configured to determine the estimated remaining longevity of the power source based on the first and second estimated longevity values, and wherein the processing circuitry is configured to indicate the determined estimated remaining longevity.

In an example, a medical device system for indicating a recommended replacement time (RRT) for a power source comprises: an implantable medical device (IMD) that comprises the power source; processing circuitry configured to determine values of a parameter of the power source, the processing circuitry configured to determine, based on determined parameter values, that the parameter reaches a pre-recommended replacement time (pre-RRT) threshold, wherein the processing circuitry is configured to start, by controlling timer circuitry and in response to determining that the parameter reaches the pre-RRT threshold, a pre-RRT to RRT timer, wherein the processing circuitry is configured to indicate the RRT in response to the earlier of the determined parameter values reaching an RRT backup threshold or the expiration of the pre-RRT to RRT timer, wherein the processing circuitry is configured to start, by controlling the timer circuitry and in response to indicating the RRT, an RRT to end of service (EOS) timer, and wherein the processing circuitry is configured to indicate EOS in response to the earlier of the determined parameter values reaching an EOS backup threshold or the expiration of the RRT to EOS timer.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

In general, this disclosure is directed to systems and techniques for determining an estimated remaining longevity of a power source of an IMD. By indicating power source events as described herein, the useable life of the power source may be extended, for example, by using the relatively large amount of energy in the second plateau of the power source voltage curve, described further herein. This subject matter described herein may allow for the use of such energy that may have previously been considered unusable due to previous shortcomings in the ability to accurately determine the remaining power source longevity (e.g., due to unpredictable characteristics when the battery is in the second plateau region or manufacturing variability). Historically, RRT has been set at a voltage threshold well above the second plateau, as described further herein, and therefore, by using the present systems and techniques, the relative lifespan of a power source may be increased for an IMD, such to avoid needless replacement procedures for a patient.

Figure 1:
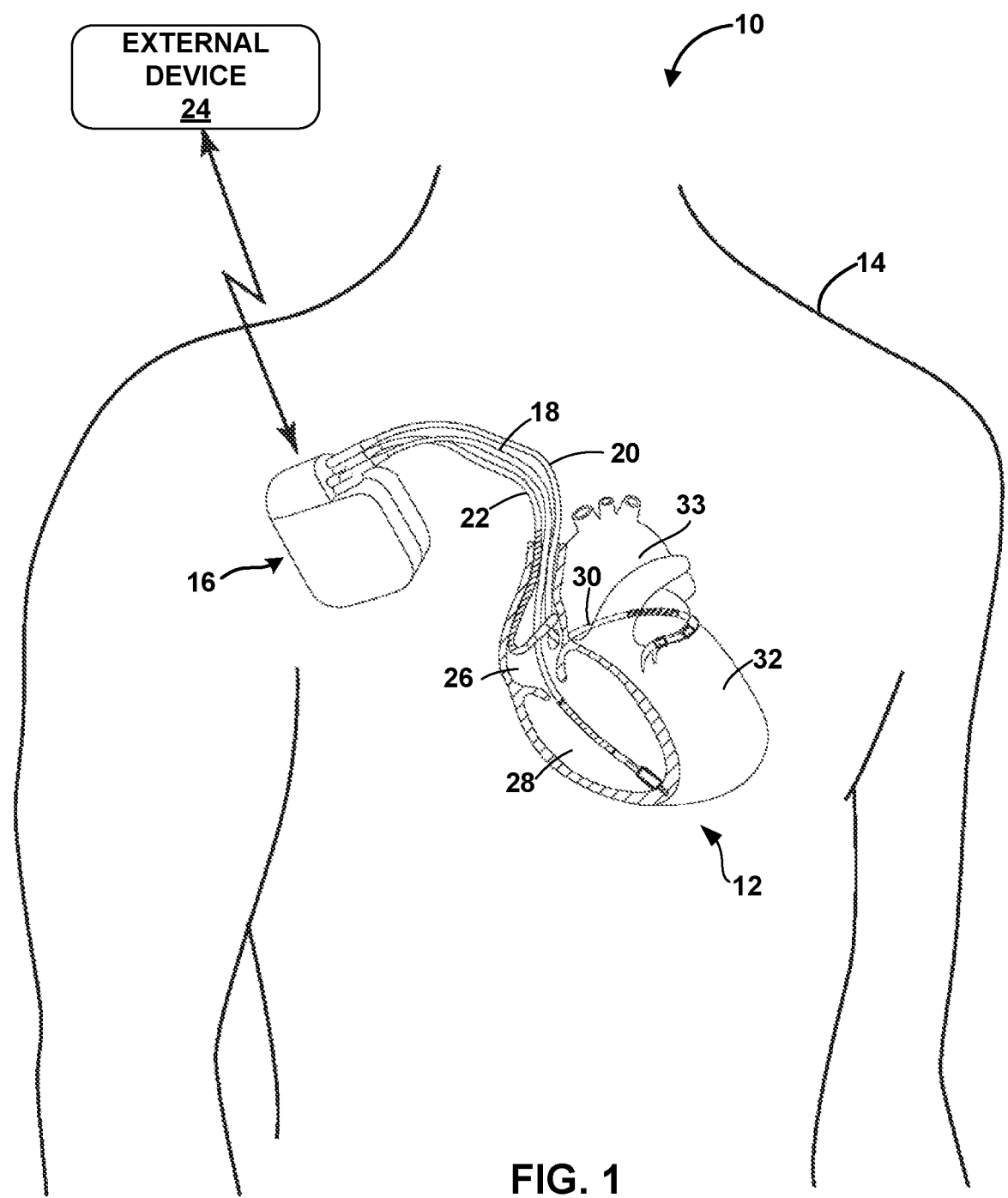
FIG. 1 is conceptual diagram illustrating an example medical device system.

FIG. 1 illustrates example medical device system 10 in conjunction with patient 14. Medical device system 10 is an example of a medical device system that is configured to implement the example techniques described herein for determining an estimated remaining longevity of the power source of the IMD (or implantable pulse generator (IPG)), and for indicating service indicators (e.g., power source events), such as RRT.

In some examples, medical device system 10 includes an implantable medical device (IMD) 16 in communication with external device 24. In the illustrated example, IMD 16 may be coupled to leads 18, 20, and 22. IMD 16 may be, for example, an implantable pacemaker that provides electrical signals to heart 12 and senses electrical activity of heart 12 via electrodes coupled to one or more of leads 18, 20, and 22. IMD 16 may provide cardiac resynchronization therapy (CRT), and may be referred to as a CRT-P device. In some examples, IMD 16 may include cardioversion or defibrillation capabilities.

Leads 18, 20, 22 extend into heart 12 of patient 14 to sense electrical activity of heart 12 and to deliver electrical stimulation to heart 12. In the example shown in FIG. 1, right ventricular (RV) lead 18 extends through one or more veins (not shown), the superior vena cava (not shown), and right atrium (RA) 26, and into RV 28. Left ventricular (LV) coronary sinus lead 20 extends through one or more veins, the vena cava, right atrium 26, and into the coronary sinus 30 to a region adjacent to the free wall of LV 32 of heart 12. Right atrial (RA) lead 22 extends through one or more veins and the vena cava, and into the RA 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 may also sense electrical signals attendant to the depolarization and repolarization of heart 12 via extravascular electrodes (e.g., electrodes positioned outside the vasculature of patient 14), such as epicardial electrodes, external surface electrodes, subcutaneous electrodes, and the like. The configurations of electrodes used by IMD 16 for sensing and pacing may be unipolar or bipolar.

IMD 16 may be configured to provide adaptive CRT to heart 12. In some examples, as part of the adaptive CRT, IMD 16 is configured to deliver at least one of fusion pacing to heart 12 and biventricular pacing to heart 12. In some examples of fusion pacing, IMD 16 may deliver a pacing stimulus (e.g., a pacing pulse) to LV 32 via electrodes of lead 20, where the pacing stimulus is timed such that an evoked depolarization of LV 32 is effected in fusion with the intrinsic depolarization of RV 28, resulting in a ventricular resynchronization. In some examples, when IMD 16 is in a biventricular pacing configuration, IMD 16 may deliver a pacing stimulus (e.g., a pacing pulse) to RV 28 via electrodes of lead 18 and a pacing stimulus to LV 32 via electrodes of lead 20 in a manner that synchronizes activation and contraction of RV 28 and LV 28.

In some examples, the adaptive CRT provided by IMD 16 may be useful for maintaining the cardiac rhythm in patient 14 with a conduction dysfunction, which may result when the natural electrical activation system of heart 12 is disrupted. The natural electrical activation system of a human heart 12 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

CRT delivered by IMD 16 may help alleviate heart failure conditions by restoring synchronous depolarization and contraction of one or more chambers of heart 12. In some cases, the fusion pacing of heart 12 described herein enhances stroke volume of a patient by improving the synchrony with which RV 28 and LV 32 depolarize and contract.

In some examples, external device 24 may be a handheld computing device or a computer workstation. External device 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, or other clinician, may interact with external device 24 to communicate with IMD 16. For example, the user may interact with external device 24 to retrieve physiological or diagnostic information from IMD 16. A user may also interact with external device 24 to program IMD 16, e.g., to select values for operational parameters of the IMD.

For example, the user may use external device 24 to retrieve information from IMD 16 regarding the rhythm of heart 12, trends therein over time, or arrhythmia episodes. As another example, the user may use external device 24 to retrieve information from IMD 16 regarding other sensed physiological parameters of patient 14, such as sensed electrical activity, activity, posture, respiration, or thoracic impedance. As another example, the user may use external device 24 to retrieve information from IMD 16 regarding the performance or integrity of IMD 16 or other components of system 10, such as leads 18, 20, and 22, or a power source of IMD 16. In In such examples, physiological parameters of patient 14 and data regarding IMD 16 may be stored in a memory of IMD 16 for retrieval by the user.

The user may use external device 24 to program a therapy progression, select electrodes used to deliver defibrillation pulses, select waveforms for the defibrillation pulse, or select or configure a fibrillation detection algorithm for IMD 16. The user may also use external device 24 to program aspects of other therapies provided by IMD 16, such as cardioversion or pacing therapies. In some examples, the user may activate certain features of IMD 16 by entering a single command via external device 24, such as depression of a single key or combination of keys of a keypad or a single point-and-select action with a pointing device.

IMD 16 and external device 24 may communicate via wireless communication using any techniques known in the art. Examples of communication techniques may include, for example, include radiofrequency (RF) telemetry, which may be an RF link established via an antenna according to Bluetooth, WiFi, or medical implant communication service (MICS), though other techniques are also contemplated. In some examples, external device 24 may include a programming head that may be placed proximate to the patient's body near the IMD 16 implant site in order to improve the quality or security of communication between IMD 16 and external device 24.

IMD 16 is an example of an IMD that may be configured to determine an estimated remaining longevity of a power source of the IMD. The systems and techniques described herein may improve the useful life of the power source of the IMD, which may be 6 months or more in some examples. External device 24 is an example of an external device that may include processing circuitry configured to indicate power source events (e.g., a RRT for the power source or an EOS for the power source). The systems and techniques described herein include indicating pre-RRT (described below), RRT, and EOS.

Figure 2:
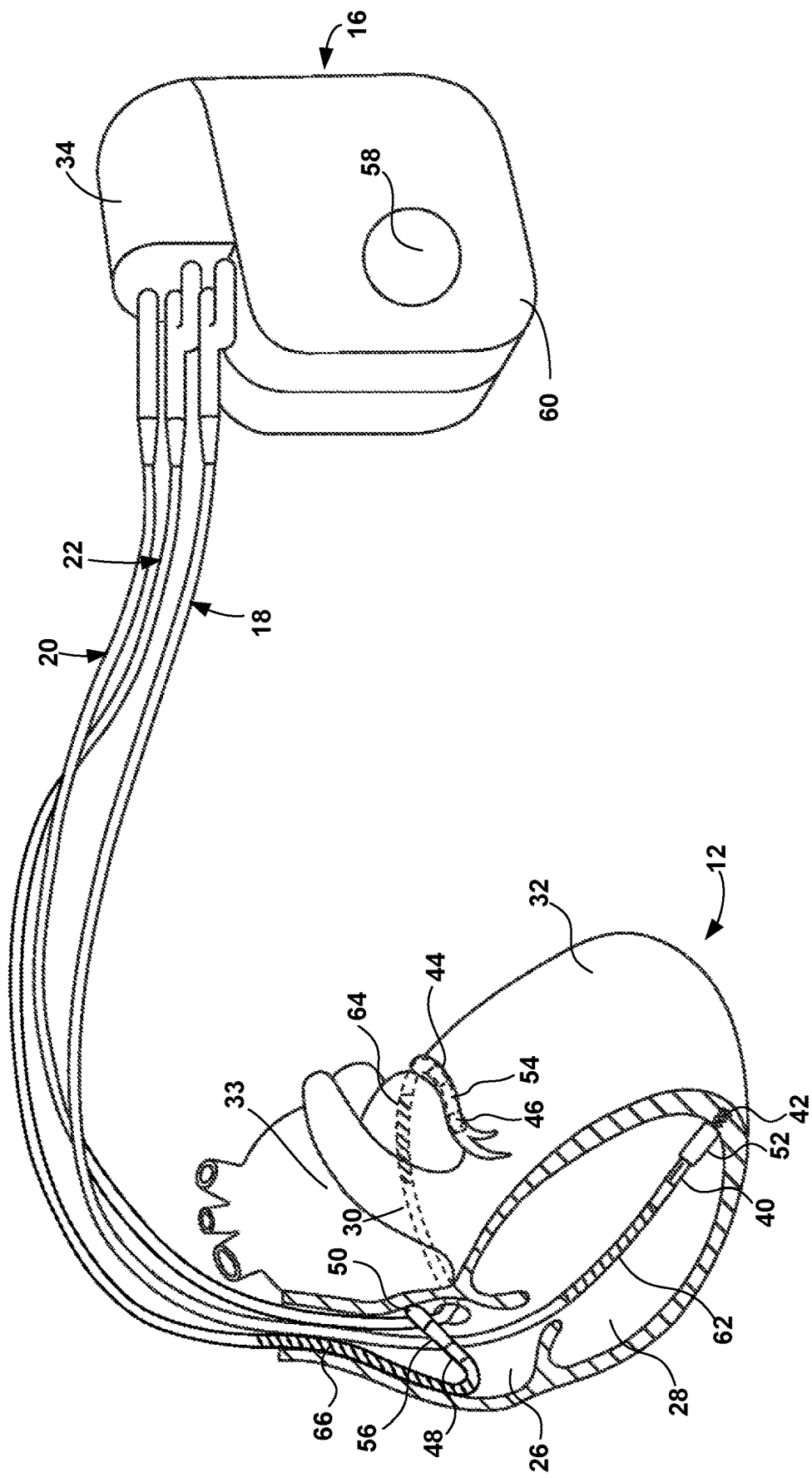
FIG. 2 is a conceptual diagram illustrating the medical device and leads of the medical device system of FIG. 1.

FIG. 2 is a conceptual diagram illustrating IMD 16 and leads 18, 20, 22 of medical device system 10 of FIG. 1 in greater detail. Leads 18, 20, 22 may be electrically coupled to therapy delivery circuitry, sensing circuitry, or other circuitry of IMD 16 via connector block 34. In some examples, proximal ends of leads 18, 20, 22 include electrical contacts that electrically couple to respective electrical contacts within connector block 34. In addition, in some examples, leads 18, 20, 22 are mechanically coupled to connector block 34 with the aid of set screws, connection pins or another suitable mechanical coupling mechanism.

Each of the leads 18, 20, 22 includes an elongated insulative lead body, which may carry a number of conductors separated from one another by tubular insulative sheaths. In the illustrated example, bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. Electrodes 40, 44, and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses to LV 32 via electrodes 44, 46 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48, and 50 may be used for unipolar sensing or stimulation delivery in combination with housing electrode 58. Housing 60 may enclose therapy delivery circuitry that generates cardiac pacing pulses and defibrillation or cardioversion shocks, as well as sensing circuitry for monitoring the patient's heart rhythm.

In some examples, leads 18, 20, 22 may also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy, or other materials known to be usable in implantable defibrillation electrodes.

The configuration of medical device system 10 illustrated in FIGS. 1 and 2 is one example, and is not intended to be limiting. In other examples, a therapy system may include extravascular electrodes, such as subcutaneous electrodes, substernal electrodes, epicardial electrodes, or patch electrodes, instead of or in addition to the electrodes of transvenous leads 18, 20, 22 illustrated in FIG. 1. Further, IMD 16 need not be implanted within patient 14. In examples in which IMD 16 is not implanted in patient 14, IMD 16 may deliver defibrillation pulses, pacing pulses, and other therapies to heart 12 via percutaneous leads that extend through the skin of patient 14 to a variety of positions within or outside of heart 12.

Figure 3:
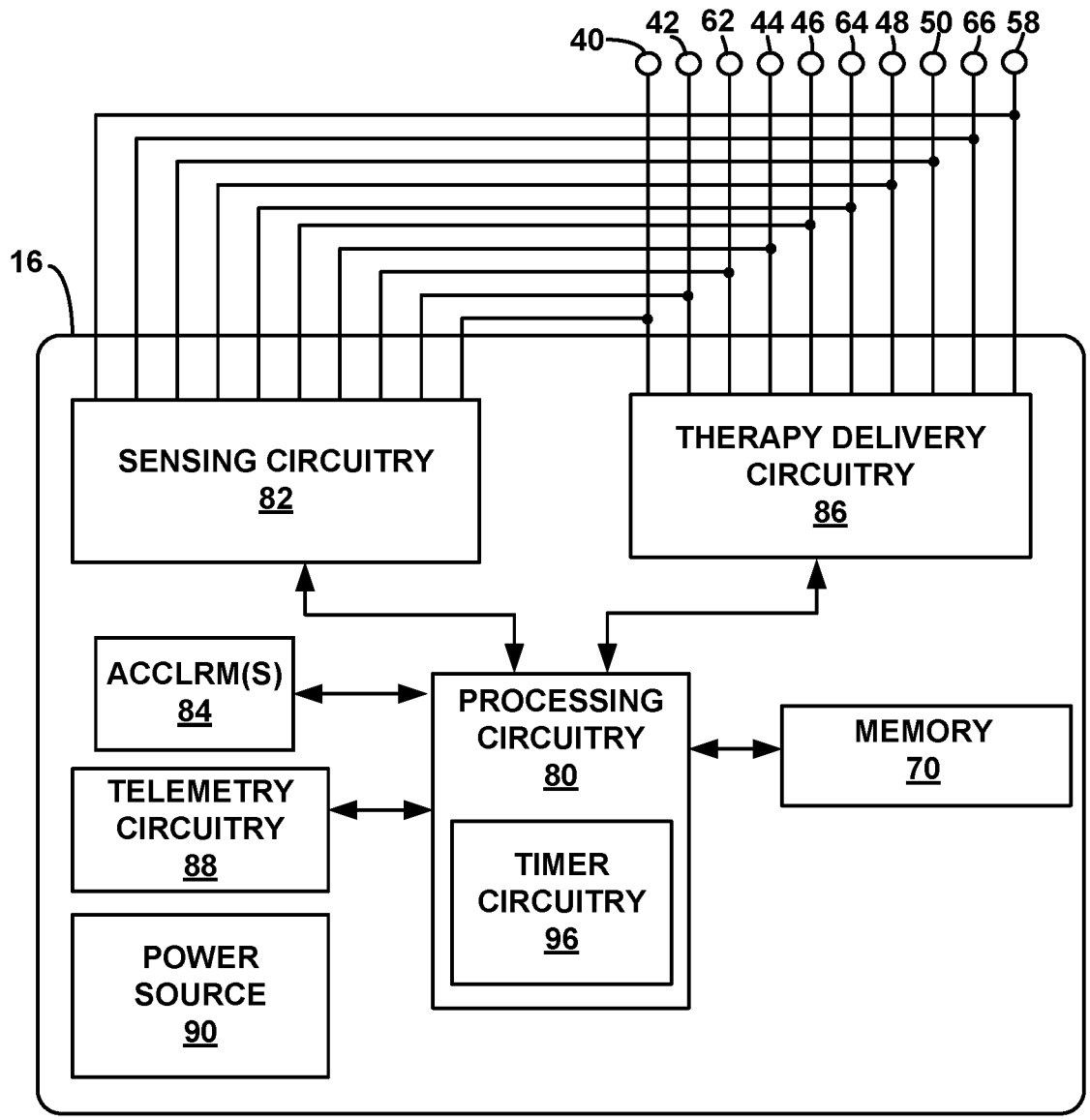
FIG. 3 is a functional block diagram of an example implantable medical device that delivers CRT to a heart of a patient.

In other examples of medical device systems that provide electrical stimulation therapy to heart 12, a therapy system may include any suitable number of leads coupled to IMD 16, and each of the leads may extend to any location within or proximate to heart 12. For example, a therapy system may include a dual chamber device rather than a three-chamber device as shown in FIG. 1. In one example of a dual chamber configuration, IMD 16 is electrically connected to a single lead that includes stimulation and sense electrodes within LV 32 as well as sense and/or stimulation electrodes within RA 26, as shown in FIG. 3. In another example of a dual chamber configuration, IMD 16 is connected to two leads that extend into a respective one of RV 28 and LV 32.

In some examples, a medical device system includes one or more intracardiac pacing devices instead of, or in addition to, an IMD coupled to leads that extend to heart 12, like IMD 16. The intracardiac pacing devices may include therapy delivery and processing circuitry within a housing configured for implantation within one of the chambers of heart 12. In such systems, the plurality of pacing devices, which may include one or more intracardiac pacing devices and/or an IMD coupled to one or more leads, may communicate to coordinate sensing and pacing in various chambers of heart 12 to provide CRT. Processing circuitry and memory of one or more of the pacing devices, and/or another implanted or external medical device, may provide the functionality for controlling delivery of CRT ascribed to processing circuitry and memory of IMD 16 herein.

Further, the techniques for power source monitoring described in this disclosure are not limited to being implemented by devices that deliver CRT or even devices for cardiac therapy and/or monitoring. For example, the techniques of this disclosure may be implemented by neurostimulation devices, or drug pumps. In general, the techniques of this disclosure may be implemented to monitor and indicate the status of a power source of any medical device.

FIG. 3 is a functional block diagram of one example configuration of IMD 16 of FIGS. 1 and 2. In the illustrated example, IMD 16 includes memory 70, processing circuitry 80, sensing circuitry 82, one or more accelerometers 84, therapy delivery circuitry 86, telemetry circuitry 88, and power source 90, one or more of which may be disposed within housing 60 of IMD 16. In some examples, memory 70 includes computer-readable instructions that, when executed by processing circuitry 80, cause IMD 16 and processing circuitry 80 to perform various functions attributed to IMD 16 and processing circuitry 80 herein. Memory 70 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. In addition to sensed physiological parameters of patient 14 (e.g., EGM or ECG signals), one or more time intervals for timing fusion pacing therapy and biventricular pacing therapy to heart 12 may be stored by memory 70.

Processing circuitry 80 may include one or more of a microprocessor, a controller, digital signal processing circuitry (DSP), an application specific integrated circuit (ASIC), a field-programmable gate array (FPGA), or equivalent discrete or integrated logic circuitry. In some examples, processing circuitry 80 may include multiple components, such as any combination of one or more microprocessors, one or more controllers, one or more DSPs, one or more ASICs, or one or more FPGAs, as well as other discrete or integrated logic circuitry. The functions attributed to processing circuitry 80 herein may be embodied as software, firmware, hardware or any combination thereof. Processing circuitry 80 may be configured to determine a heart rate of heart 12 based on electrical activity sensed by sensing circuitry 82.

Processing circuitry 80 may determine one or more operational parameters of IMD 16. For example, power operational modes may be determined (e.g., low, medium, or high power modes). In an example, an IMD operational parameter may include a program, such as type of stimulation being provided (e.g., cardioversion or defibrillation). In an example, such a parameter may include a pulse width, pacing amplitude, pacing rate, pacing percentages, or any combination described herein. These parameters may be used by processing circuitry 80 in calculating the estimated longevity values described herein.

Sensing circuitry 82 is configured to monitor signals from at least one of electrodes 40, 42, 44, 46, 48, 50, 58, 62, 64 or 66 in order to monitor electrical activity of heart 12, such as via EGM signals. For example, sensing circuitry 82 may sense atrial events (e.g., a P-wave) with electrodes 48, 50, 66 within RA 26 or sense an LV 32 event (e.g., an R-wave) with electrodes 44, 46, 64 within LV 32. In some examples, sensing circuitry 82 includes switching circuitry to select which of the available electrodes are used to sense the electrical activity of heart 12. For example, processing circuitry 80 may select the electrodes that function as sense electrodes via the switching circuitry within sensing circuitry 82 (e.g., by providing signals via a data/address bus). In some examples, sensing circuitry 82 includes one or more sensing channels, each of which may comprise an amplifier. In response to the signals from processing circuitry 80, the switching circuitry of sensing circuitry 82 may couple the outputs from the selected electrodes to one of the sensing channels.

In some examples, one channel of sensing circuitry 82 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, the R-wave amplifiers may take the form of an automatic gain controlled amplifier that provides an adjustable sensing threshold as a function of the measured R-wave amplitude of the heart rhythm. In addition, in some examples, one channel of sensing circuitry 82 may include a P-wave amplifier that receives signals from electrodes 48 and 50, which are used for pacing and sensing in RA 26 of heart 12.

In some examples, sensing circuitry 82 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 70 as an EGM. In some examples, the storage of such EGMs in memory 70 may be under the control of a direct memory access circuit. Processing circuitry 80 may employ digital signal analysis techniques to characterize the digitized signals stored in memory 70 to detect and classify the patient's heart rhythm from the electrical signals. Processing circuitry 80 may detect and classify the heart rhythm of patient 14 by employing any of the numerous signal processing methodologies known in the art.

Signals generated by sensing circuitry 82 may include, for example: an RA-event signal, which indicates a detection of a P-wave via electrodes implanted within RA 26 (FIG. 1); an LA-event signal, which indicates a detection of a P-wave via electrodes implanted within left atrium (LA) 33 (FIG. 1); an RV-event signal, which indicates a detection of an R-wave via electrodes implanted within RV 28; or an LV-event signal, which indicates a detection of an R-wave via electrodes implanted within LV 32. In the example of system 10 shown in FIGS. 1 and 2, IMD 16 is not connected to electrodes that are implanted within LA 33. However, in other example therapy systems, IMD 16 may be connected to electrodes that are implanted within LA 33 in order to sense electrical activity of LA 33.

In some examples, IMD 16 may include one or more additional sensors, such as accelerometers 84. In some examples, accelerometers 84 may comprise one or more three-axis accelerometers. Signals generated by accelerometers 84 may be indicative of, for example, gross body movement of patient 14, such as a patient posture or activity level. Regardless of the configuration of accelerometers 84, processing circuitry 80 may determine patient parameter values based on the signals obtained therefrom. Accelerometers 84 may produce and provide signals to processing circuitry 80 for a determination as to the posture and activity level of patient 14 at a given time. Processing circuitry 80 may then use the determined posture and activity level to further determine whether patient 14 is awake or asleep, and, if patient 14 is determined to be awake, to further determine whether patient 14 is at rest or exercising.

Therapy delivery circuitry 86 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Therapy delivery circuitry 86 is configured to generate and deliver electrical stimulation therapy. For example, therapy delivery circuitry 86 may deliver a pacing stimulus to LV 32 (FIG. 2) of heart 12, in accordance with the fusion pacing techniques described herein, via at least two electrodes 44, 46 (FIG. 2). As another example, therapy delivery circuitry 86 may deliver a pacing stimulus to RV 28 via at least two electrodes 40, 42 (FIG. 2) and a pacing stimulus to LV 32 via at least two electrodes 44, 46 (FIG. 2), e.g., in accordance with the biventricular pacing techniques described herein.

In some examples, therapy delivery circuitry 86 is configured to deliver cardioversion or defibrillation shocks to heart 12. The pacing stimuli, cardioversion shocks, and defibrillation shocks may be in the form of stimulation pulses. In other examples, therapy delivery circuitry 86 may deliver one or more of these types of stimulation in the form of other signals, such as sine waves, square waves, or other substantially continuous time signals.

Therapy delivery circuitry 86 may include a switching circuitry, and processing circuitry 80 may use the switching circuitry to select, e.g., via a data/address bus, which of the available electrodes are used to deliver defibrillation pulses or pacing pulses. The switching circuitry may include a switch array, switch matrix, multiplexer, or any other type of switching device suitable to selectively couple stimulation energy to selected electrodes. In other examples, processing circuitry 80 may select a subset of electrodes 40, 42, 44, 46, 48, 50, 58, 62, 64, and 66 with which stimulation is delivered to heart 12 without a switching circuitry.

Processing circuitry 80 includes timer circuitry 96, which may be embodied as hardware, firmware, software, or any combination thereof. In some examples, processing circuitry 80 is coupled to timer circuitry 96. Timer circuitry 96 may comprise a dedicated hardware circuit, such as an ASIC, separate from other processing circuitry 80 components, such as a microprocessor, or a software module executed by a component of processing circuitry 80 (e.g., a microprocessor or ASIC). Timer circuitry 96 may help control the delivery of pacing pulses to heart 12. Timer circuitry 96 may be configured to determine time stamps of events, determine durations between events, and start and end timers (e.g., countdowns).

In examples in which IMD 16 delivers a pacing pulse according to the one or more A-V interval values selected and/or determined by processing circuitry 80, timer circuitry 96 may include a timer for determining that a selected A-V interval has elapsed after processing circuitry 80 determines that an atrial pace or sense event (Apis, or more generally A) has occurred. The timer circuitry 96 may be configured to begin upon the detection of the preceding atrial pace or sense event (Apis) by processing circuitry 80. Upon expiration of the particular timer, processing circuitry 80 may control therapy delivery circuitry 86 to deliver a pacing stimulus, according to a fusion or biventricular pacing configuration, to heart 12. For example, timer circuitry 96 may generate a trigger signal that triggers the output of a pacing pulse by therapy delivery circuitry 86.

Therapy delivery circuitry 86 may deliver cardioversion or defibrillation shock with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching circuitry of therapy delivery circuitry 86.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide the data to be uplinked to external device 24 and the control signals for the telemetry circuit within telemetry circuitry 88, e.g., via an address/data bus. In some examples, telemetry circuitry 88 may provide received data to processing circuitry 80 via a multiplexer.

In some examples, processing circuitry 80 may transmit atrial and ventricular heart signals (e.g., EGM signals) produced by atrial and ventricular sense amp circuits within sensing circuitry 82 to external device 24. Other types of information may also be transmitted to external device 24, such as the various intervals and delays used to deliver CRT. External device 24 may interrogate IMD 16 to receive the heart signals. Processing circuitry 80 may store heart signals within memory 70, and retrieve stored heart signals from memory 70.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide the data to be uplinked to external device 24 and the control signals for the telemetry circuit within telemetry circuitry 88 (e.g., via an address/data bus). In some examples, telemetry circuitry 88 may provide received data to processing circuitry 80 via a multiplexer.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis. In some examples, power source 90 may comprise a silver vanadium oxide (SVO) and lithium/carbon monofloride Li/CFx hybrid cathode battery, such as used in IMDs (e.g., pacemakers and defibrillators). In some examples, power source 90 may comprise a generally low impedance battery such as lithium magnesium dioxide (LiMnO2) or lithium silver vanadium oxide (LiSVO). Power source 90 may exhibit a relatively long flat plateau (e.g., the second plateau as described with respect to FIGS. 7, 8, and 9) near the end of service of power source 90. By indicating power source events as described herein, the useable life of power source 90 may be extended, for example, by using the relatively large amount of energy in the second plateau.

In some examples, processing circuitry 80 may determine values of one or more parameters of power source 90. For example, processing circuitry may estimate current drain, determine historical voltage levels, such as stored in memory 70, an instantons voltage level, an average voltage (e.g., over three days), or any combination of parameters described herein.

In some examples, processing circuitry 80 may be configured to control timer circuitry 96 to determine a duration, a time stamp, or control a timer or countdown. An example of a replacement indicator timer for IMDs is described in U.S. Patent Application Publication No. 2007/0150018 by Betzold et al., which is entitled "REPLACEMENT INDICATOR TIMER FOR IMPLANTABLE MEDICAL DEVICES" and is incorporated herein by reference in its entirety.

In some examples, the techniques described herein include calculating estimated durations until the power source (e.g., power source 90) reaches a particular service indicator, such as RRT backup or EOS, as described herein. An example of estimating remaining battery service life for IMDs is described in U.S. Pat. No. 8,612,167 to Schmidt et al., which is entitled "ESTIMATING REMAINING BATTERY SERVICE LIFE IN AN IMPLANTABLE MEDICAL DEVICE" and is incorporated herein by reference in its entirety.

Figure 4:
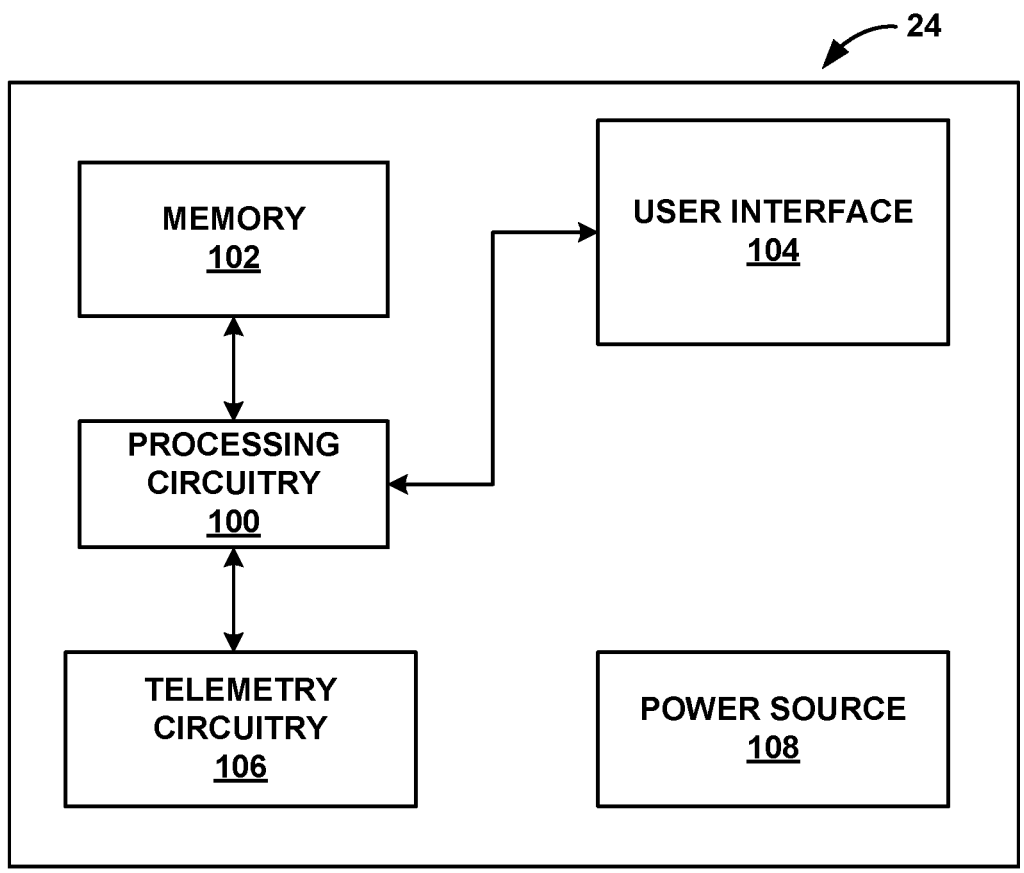
FIG. 4 is a functional block diagram of an example external device.

FIG. 4 is functional block diagram of an example external device 24. As shown in FIG. 4, external device 24 includes processing circuitry 100, a memory 102, a user interface 104, telemetry circuitry 106, and a power source 108. External device 24 may be a dedicated hardware device with dedicated software for interacting with IMD 16. Alternatively, external device 24 may be an off-the-shelf computing device running an application that enables external device 24 to interact with IMD 16.

A user may use external device 24 to select programmable parameters that control the monitoring and delivery of therapy by IMD 16, and to retrieve information collected by IMD regarding the condition of patient 14 or the performance of IMD 16. The user may interact with external device 24 via user interface 104, which may include display to present graphical user interface to a user, and a keypad or another mechanism for receiving input from a user.

Processing circuitry 100 can take the form one or more microprocessors, DSPs, ASICs, FPGAs, programmable logic circuitry, or the like, and the functions attributed to processing circuitry 100 herein may be embodied as hardware, firmware, software, or any combination thereof.

Memory 102 may store instructions that cause processing circuitry 100 to provide the functionality ascribed to external device 24 herein, and information used by processing circuitry 100 to provide the functionality ascribed to external device 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before external device 24 is used to program therapy for another patient. Memory 102 may also store information that controls therapy delivery by IMD 16, such as stimulation parameter values.

External device 24 may communicate wirelessly with IMD 16, such as using RF communication or proximal inductive interaction. This wireless communication is possible through the use of telemetry circuitry 106, which may be coupled to an internal antenna or an external antenna. An external antenna that is coupled to external device 24 may correspond to the programming head that may be placed over heart 12, as described above with reference to FIG. 1.

Telemetry circuitry 106 may be similar to telemetry circuitry 88 of IMD 16 (FIG. 3). Telemetry circuitry 106 may also be configured to communicate with another computing device via wireless communication techniques, or direct communication through a wired connection. Examples of local wireless communication techniques that may be employed to facilitate communication between external device 24 and another computing device include RF communication according to the 802.11 or Bluetooth specification sets, infrared communication, e.g., according to the IrDA standard, or other standard or proprietary telemetry protocols. In this manner, other external devices may be capable of communicating with external device 24 without needing to establish a secure wireless connection.

Power source 108 is configured to deliver operating power to the components of external device 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 24. In other embodiments, traditional batteries (e.g., nickel cadmium or lithium ion batteries) may be used. In addition, external device 24 may be directly coupled to an alternating current outlet to power external device 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In some examples, processing circuitry 100 and memory 102 of external device 24 may be configured to provide some or all of the functionality ascribed to processing circuitry 80 and memory 70 of IMD 16. For example, processing circuitry 100 may be configured with the same or similar functionality as processing circuitry 80, such as for determining an estimated longevity of the power source or indicating power source events. In some examples, processing circuitry 100 may receive data from a memory (e.g., memory 70 of IMD 16 or memory 102 of external device 24), such as via telemetry circuitry 88 of IMD 16 and/or telemetry circuitry 106 of external device 24. In an example, processing circuitry 100 may receive IMD and/or power source information (e.g., voltage signals indicative of the voltage of a power source, such as power source 90 of IMD 16, over time). Processing circuitry 100 may determine whether the voltage signals meet thresholds and/or determine calculations of estimated longevity values of the power, as described further herein. In some examples, processing circuitry 100 may provide an indication (e.g., of a service indicator or an estimated remaining longevity of the power source) to a user, such as via user interface 104.

Figure 5:
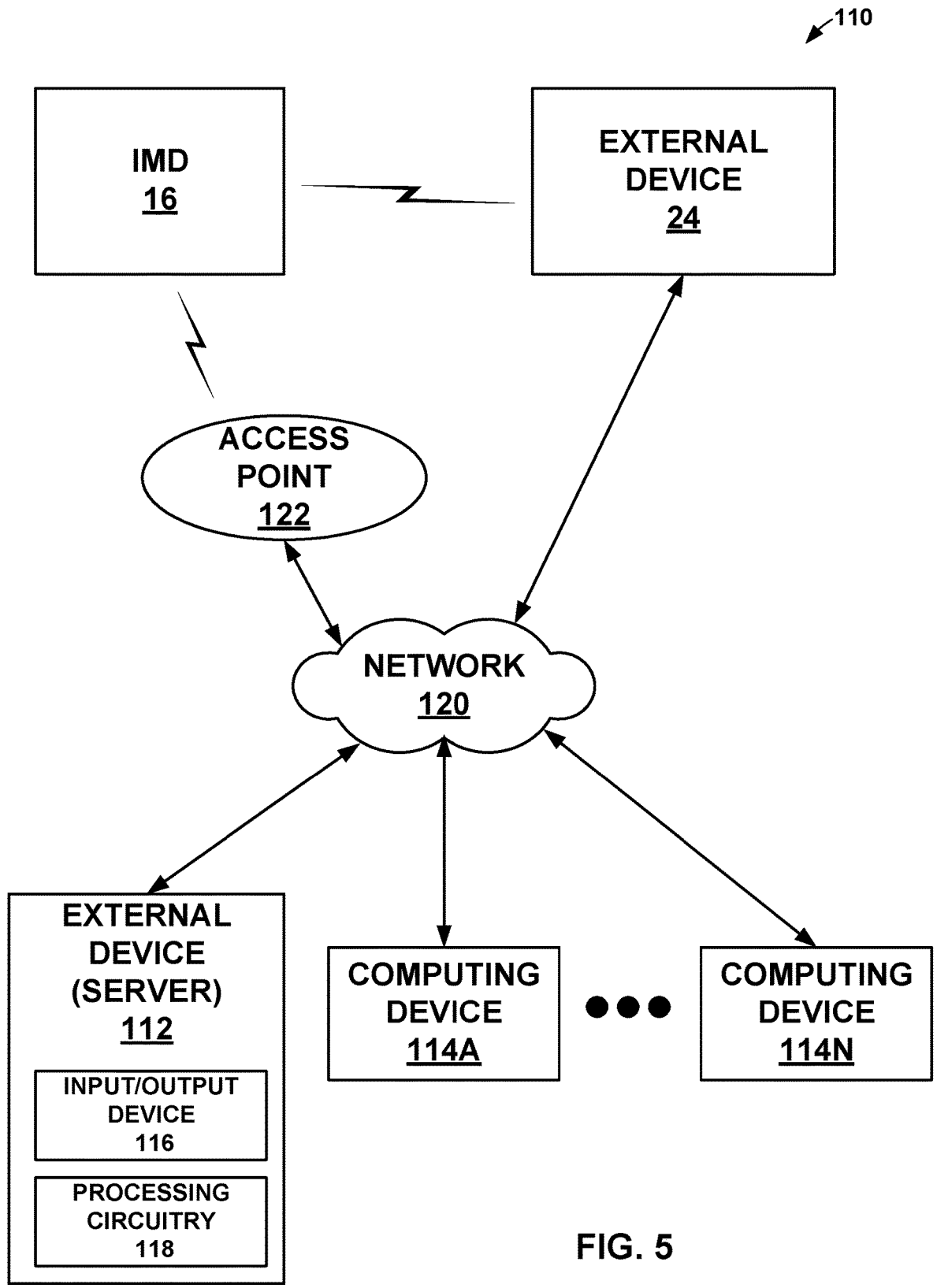
FIG. 5 is a block diagram illustrating an example system that includes an external device, such as a server, and one or more computing devices that are coupled to the IMD and external device shown in FIG. 1 via a network.

FIG. 5 is a block diagram illustrating a system 110 that includes an external device 112, such as a server, and one or more computing devices 114A-114N that are coupled to IMD 16 and external device 24 shown in FIG. 1 via a network 120, according to one example. In this example, IMD 16 uses telemetry circuitry 88 (FIG. 3) to communicate with external device 24 via a first wireless connection, and to communicate with an access point 122 via a second wireless connection. In the example of FIG. 5, access point 122, external device 24, external device 112, and computing devices 114A-114N are interconnected, and able to communicate with each other, through network 120. In some cases, one or more of access point 122, external device 24, external device 112, and computing devices 114A-114N may be coupled to network 120 through one or more wireless connections. IMD 16, external device 24, external device 112, and computing devices 114A-114N may each comprise one or more processing circuitries, such as one or more microprocessors, DSPs, ASICs, FPGAs, programmable logic circuitry, or the like, that may perform various functions and operations, such as those described herein.

Access point 122 may comprise a device that connects to network 120 via any of a variety of connections, such as telephone dial-up, digital subscriber line (DSL), or cable modem connections. In other examples, access point 122 may be coupled to network 120 through different forms of connections, including wired or wireless connections. In some examples, access point 122 may communicate with external device 24 and/or IMD 16. Access point 122 may be co-located with patient 14 (e.g., within the same room or within the same site as patient 14) or may be remotely located from patient 14. For example, access point 122 may be a home monitor that is located in the patient's home or is portable for carrying with patient 14.

During operation, IMD 16 may collect, measure, and store various forms of diagnostic data. For example, IMD 16 may collect ECG and/or EGM signals, and determine different CRT configurations and A-V intervals. In certain cases, IMD 16 may directly analyze collected diagnostic data and generate any corresponding reports or alerts. In some cases, however, IMD 16 may send diagnostic data to external device 24, access point 122, and/or external device 112, either wirelessly or via access point 122 and network 120, for remote processing and analysis.

For example, IMD 16 may send external device 24 data that indicates whether a loss of intrinsic AV conduction was detected. External device 24 may generate reports or alerts after analyzing the data. As another example, IMD 16 may send a system integrity indication generated by processing circuitry 80 (FIG. 3) to external device 24, which may take further steps to determine whether there may be a possible condition with one or more of leads 18, 20, and 22. For example, external device 24 may initiate lead impedance tests or IMD 16 may provide lead impedance information, if such information is already available.

In another example, IMD 16 may provide external device 112 with collected EGM data, system integrity indications, and any other relevant physiological or system data via access point 122 and network 120. External device 112 includes one or more processing circuitries 118. In some cases, external device 112 may request such data, and in some cases, IMD 16 may automatically or periodically provide such data to external device 112. Upon receipt of the diagnostic data via input/output device 116, external device 112 is capable of analyzing the data and generating reports or alerts upon determination that there may be a possible condition with one or more of leads 18, 20, and 22 or with patient 14.

In one example, external device 112 may comprise a secure storage site for information that has been collected from IMD 16 and/or external device 24. In this example, network 120 may comprise an Internet network; and trained professionals, such as clinicians, may use computing devices 114A-114N to securely access stored data on external device 112. For example, the trained professionals may need to enter usernames and passwords to access the stored information on external device 112. In one example, external device 112 may be a remote patient monitoring system, such as the Medtronic® CareLink® Network developed by Medtronic plc, of Dublin, Ireland.

In some examples, processing circuitry and memory of one or more of access point 122, server 112, or computing devices 114 (e.g., processing circuitry 118 and memory of server 112, may be configured to provide some or all of the functionality ascribed to processing circuitry 80 and memory 70 of IMD 16. For example, server 112 may be configured to store one or more of templates or historical voltage values of the power source 90, or thresholds for power source service indicators, as described below. In some examples, processing circuitry 118 may receive data from memory 70 of IMD 16, such as via telemetry circuitry 88 of IMD 16 and input/output device 116 of external device 112. In an example, processing circuitry 118 may receive voltage signals indicative of the voltage of a power source (e.g., power source 90 of IMD 16) over time. Processing circuitry 118 may determine whether the voltage signals meet thresholds and/or determine calculations of estimated longevity values of the power, as described further herein. In some examples, processing circuitry 118 may provide an indication (e.g., of a service indicator or an estimated remaining longevity of the power source) to a user, such as via one or more of computing devices 114A-114N.

Figure 6:
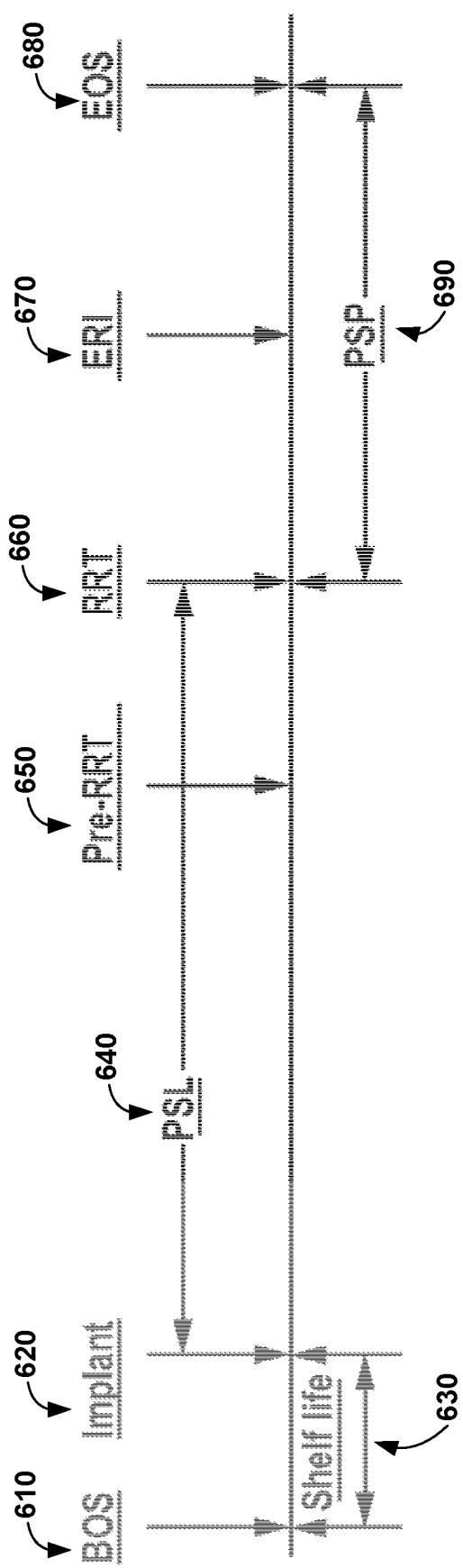
FIG. 6 is a conceptual diagram illustrating relations of events, such as power source service indicators.

FIG. 6 is a conceptual diagram illustrating relations of events, such as power source service indicators. For example, Beginning of Service (BOS) 610 may be indicated when an individual device is first released by the manufacturer as fit for placing on the market. The device may be implanted at the implant 620 mark, and the shelf life 630 is the period between BOS 610 and implant 620.

End of Service (EOS) 680 may be indicated when the Prolonged Service Period (PSP) 690 has elapsed and performance to design specifications cannot be assured. PSP 690 may be the period beyond the RRT 660 during which the IMD continues to function as defined by the manufacturer to prolong basic bradyarrhythmia pacing.

Projected Service Life (PSL) 640 may be the period from the implantation of the IMD to the Recommended Replacement Time (RRT) 660 under defined conditions. RRT 660 may be indicated when the power source indicator reaches the value set by the manufacturer of the IMD for its recommended replacement. RRT may also indicate entry into the PSP 690.

Elective Replacement Indicator (EM) 670 may be a secondary indicator which is intended to inform the user that there are less than 90 days of device service remaining. ERI 670 is not a Commission Européenne de Normalisation Électrique (CENELEC) definition.

Pre-Recommended Replacement Time (pre-RRT) 650 is not a CENELEC definition (e.g., pre-RRT 650 may be used internally by system 10, for example), and it is not necessarily shown to the user. Pre-RRT 650 may indicate that the power source voltage is transitioning from the first plateau to the second plateau.

Figure 7:
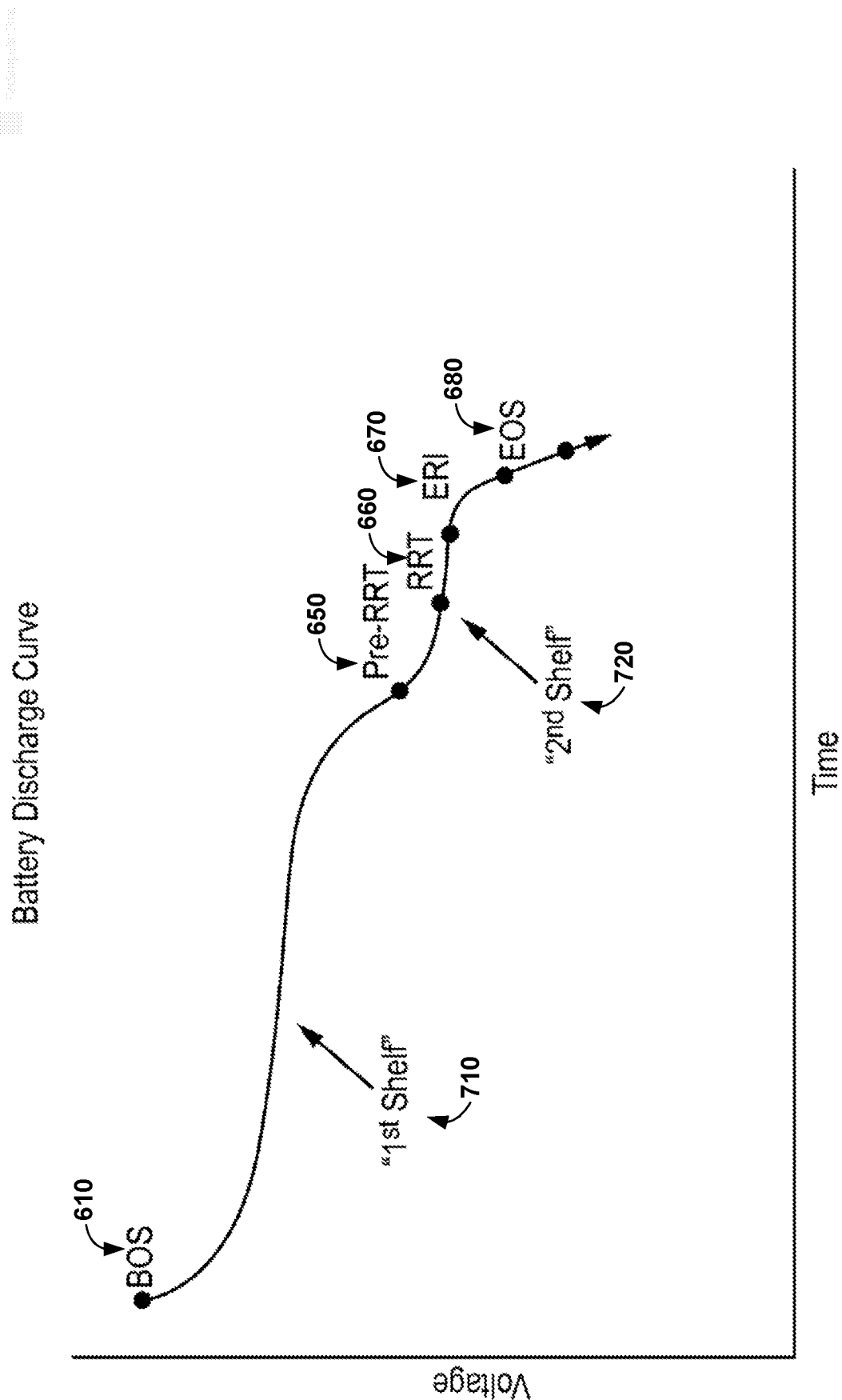
FIG. 7 is a conceptual graph of a battery discharge curve illustrating power source service indicators.

The times of occurrences of these defined events relative to an exemplary battery discharge curve are illustrated in FIG. 7. The first shelf or plateau extends for a certain time period until the battery discharge curve quickly decreases while the second shelf or plateau extends a shorter time period, as shown in FIG. 7.

FIG. 7 is a conceptual graph of a battery discharge curve illustrating power source service indicators of the example of FIG. 6. For example, a 1st shelf 710 (e.g., first plateau 710) and a 2nd shelf 720 (e.g., second plateau 720) are shown relative to example power source indications (e.g., BOS 610, pre-RRT 650, RRT 660, ERI 670, and EOS 680). After EOS 680, the power source may not have the ability to sufficiently power the circuits of the 1 MB.

Figure 8:
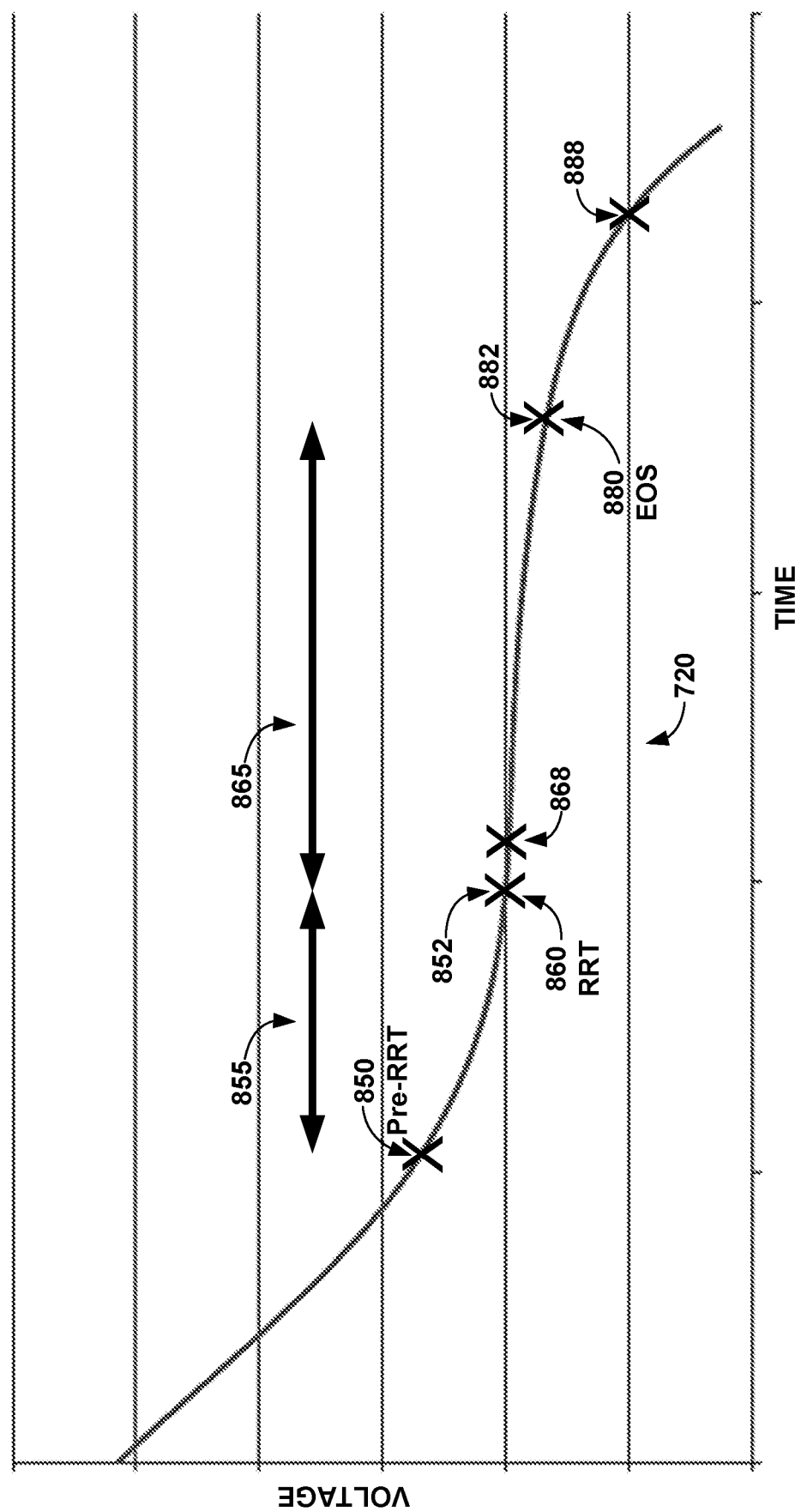
FIG. 8 is a conceptual graph of a power source voltage depletion curve, according to an example of this disclosure.

FIG. 8 is a conceptual graph of a power source voltage curve (e.g., a battery discharge curve), according to an example of this disclosure. An example second plateau 720 is shown in FIG. 8. The example of FIG. 8 illustrates techniques for indicating a power source (e.g., power source 90 of FIG. 3) events (e.g., RRT or EOS). For example, processing circuitry (e.g., processing circuitry 80, 100, or 118) may determine values of a parameter of the power source. The parameter may be a voltage, such as an instantaneous voltage, in some examples. In an example, the parameter is an average voltage, such as measured over a period of days (e.g., 1 to 5 days, such as 3 days). Similarly, the parameter may be a current usage at certain times or over time, a rate of battery depletion, historical depletions (e.g., before recharging the power source), template depletion curves (e.g., the first and second plateau curves as described herein), or another parameter or combination of parameters.

The processing circuitry may be configured to determine, based on the determined parameter values of the power source that the parameter reaches a pre-RRT threshold. In the example of FIG. 8, the pre-RRT threshold may be about 2.625 volts, and the processing circuitry may indicate pre-RRT 850 at the time that corresponds to the event. In other examples, the pre-RRT threshold may be more or less than 2.625 volts, such as from 2.615 to 2.635 volts. Other values may be used for the pre-RRT threshold.

In response to determining that the parameter (e.g., voltage) reaches the pre-RRT threshold, the processing circuitry may control timer circuitry (e.g., timer circuitry 96) to start a pre-RRT to RRT timer. In the example of FIG. 8, the pre-RRT to RRT timer 855 is shown as extending from pre-RRT 850 to the expiration 852 of pre-RRT to RRT timer 855. RRT backup 868 threshold is illustrated as occurring after expiration 852 in this example. In some examples, RRT is indicated to be the earlier of the expiration 852 of the pre-RRT to RRT timer 855 or the time at which RRT backup 868 threshold is reached. In the example of FIG. 8, RRT 860 is indicated at the expiration 852 of the pre-RRT to RRT timer 855, which may be before the RRT backup 868 threshold. The RRT backup 868 voltage threshold may be about 2.600 volts. In some examples, the RRT backup 868 threshold may be more or less than 2.600 volts. In some examples, RRT backup 868 is set to be within the second plateau 720.

In response to indicating RRT 860, the processing circuitry may be configured to start an RRT to EOS timer 865. The figures may not necessarily be drawn to scale, and therefore, although pre-RRT to RRT timer 855 may appear shorter than RRT to EOS timer 865, they may both be the same or similar durations. In other examples, the timers of the example of FIG. 8 may have different durations. Each of timer 855 and timer 865, as described with respect to FIG. 8, may have any desirable duration (e.g., less than 90 days, 90 days, 180 days, or more than 180 days). The processing circuitry may be configured to indicate EOS in response to the earlier of the expiration of the RRT to EOS timer 865 or the parameter reaching an EOS backup 888 threshold voltage. Thus, in this example, EOS 880 is indicated at the time corresponding to the expiration 882 of the RRT to EOS timer 865.

RRT 860 and/or EOS 880 may therefore be indicated by the processing circuitry before the respective preceding timer, depending on the particular curve of the depletion of the power source.

Figure 9:
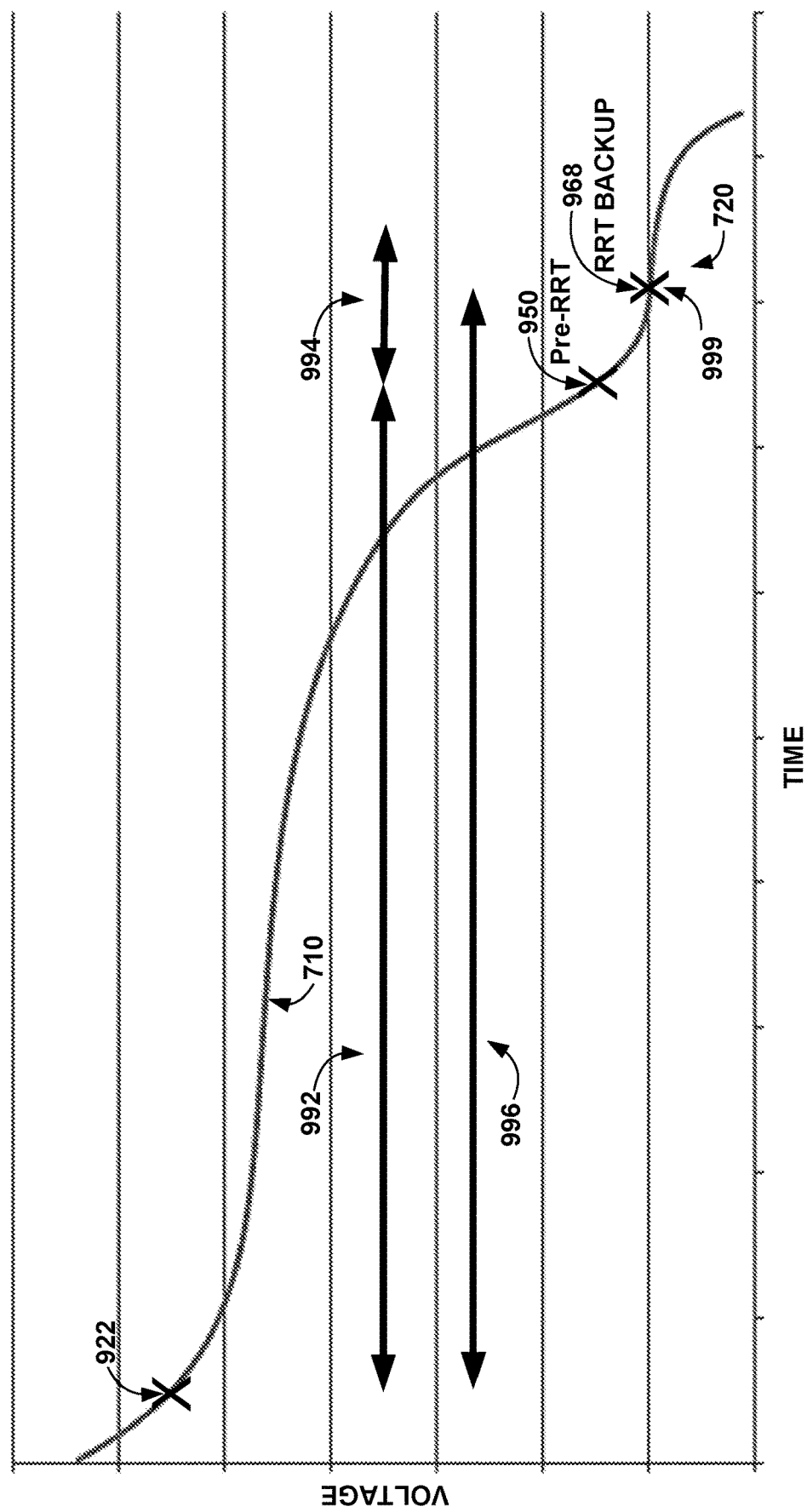
FIG. 9 is a conceptual graph of a power source voltage depletion curve, according to an example of this disclosure.

FIG. 9 is a conceptual graph of a power source voltage depletion curve, according to an example of this disclosure. Examples of the first plateau 710 and the second plateau 720 are shown in FIG. 9. The example of FIG. 9 illustrates techniques for determining an estimated remaining longevity of a power source (e.g., power source 90) of an IMD. Instant time 922 may represent a time and corresponding voltage value of a present time (e.g., a time from which the estimated remaining longevity of the power source is measured). Processing circuitry may be configured to determine one or more parameters of the power source and one or more operational parameters of the IMD (e.g., IMD 16), as described herein.

Based on at least some of the determined parameter values, the processing circuitry may be configured to calculate a first estimated duration 992 until one of the determined parameters of the power source (e.g., the voltage or another described above) reaches a pre-RRT threshold 950. The processing circuitry may add a timer duration 994 to the first estimated duration 992 to determine a first estimate longevity value (e.g., the duration from instant time 922 to the expiration of timer duration 994).

Based on the at least some of the determined parameter values (e.g., of the power source and/or the IMD), the processing circuitry may be configured to calculate a second estimated duration 996 until one of the determined parameters of the power source reaches an RRT backup threshold 968. The processing circuitry may determine the second estimate duration 996 to be a second estimated longevity value.

In the example of FIG. 9, the processing circuitry may be configured to determine the estimated remaining longevity of the power source based on the first and second estimated longevity values. In some examples, the processing circuitry compares the first and second estimated longevity values. The processing circuitry may determine that the smaller of the first and second estimated remaining longevity values is used as the estimated remaining longevity of the power source. For example, as shown in FIG. 9, the estimated remaining longevity end time corresponds to point 999, where the estimated remaining longevity spans from instant time 922 to point 999. The processing circuitry may be configured to indicate (e.g., via a notification) the determined estimated remaining longevity.

In other examples, the processing circuitry may determine another estimated remaining longevity value is used as the estimated remaining longevity of the power source. For example, the processing circuitry may indicate that the larger of the first and second estimated remaining longevity values is used. In an example, the processing circuitry may indicate that an average of the first and second estimated remaining longevity values is used. In an example, the processing circuitry may use a function, such as may include one or more weighting factors, based on the first and second estimated remaining longevity values as the estimated remaining longevity of the power source. These and other examples of determining the estimated remaining longevity of the power source may be used in any combination.

In some examples, the processing circuitry determines the estimated remaining longevity before pre-RRT is indicated (e.g., at instant time 922). In other examples, such as when the instant time occurs during timer duration 994, the processing circuitry determines the estimated remaining longevity to be the smaller of a remaining duration of timer duration 994 or the duration until the second estimated longevity value (e.g., the RRT backup 968 time).

In some examples, the one or more operational parameters of the implantable medical device may be at least one of a depth of discharge, a stimulation parameter, or a bioelectrical sensing parameter. Timer duration 994 may be 180 days, or any other duration described herein.

In the examples of FIGS. 8 and 9, the horizontal axis is time, such as may be measured in days, weeks, months, or years, and the vertical axis is shown as voltage, although the vertical axis in other examples may be another parameter of the power source as described herein.

Figure 10:
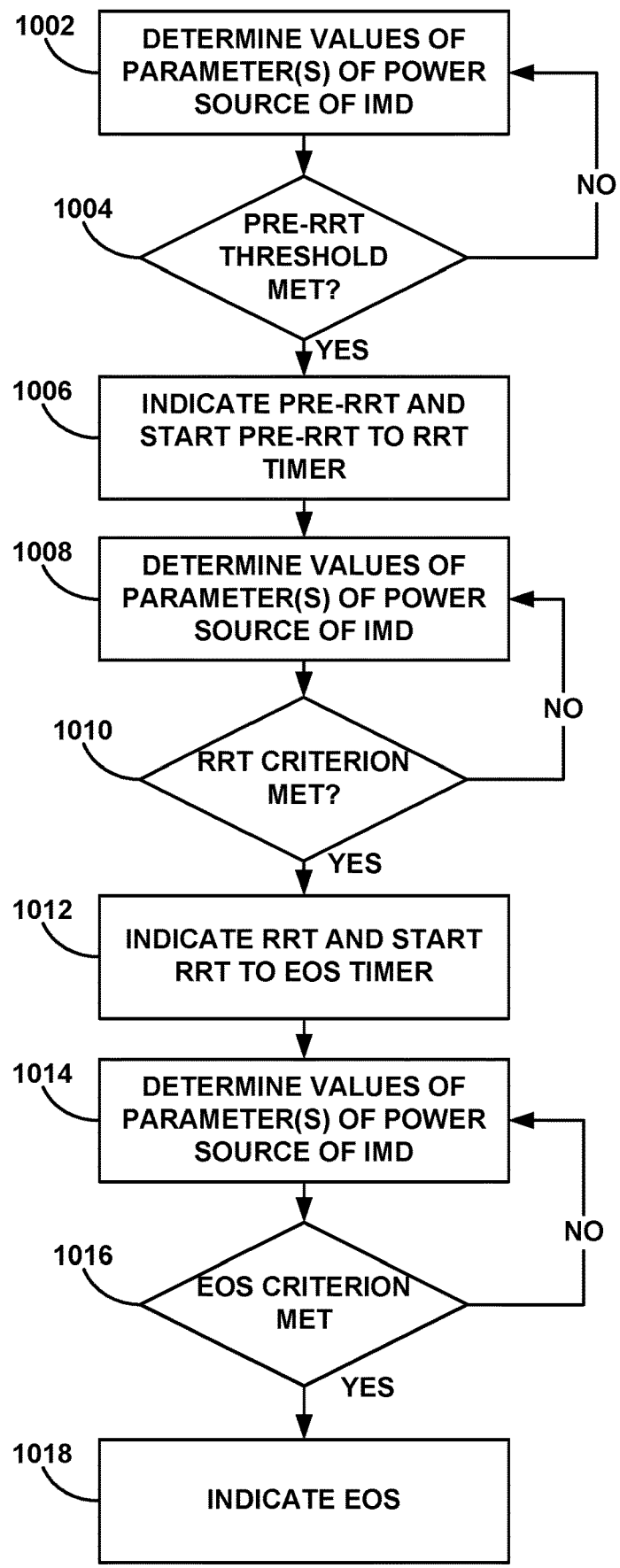
FIG. 10 is a flow diagram illustrating an example technique for indicating RRT for a power source.

FIG. 10 is a flow diagram illustrating an example technique for indicating RRT for a power source. In some examples, an IMD (e.g., IMD 16 of FIG. 1, such as via processing circuitry 80) may determine values of one or more parameters of the power source of the IMD (1002). As described with respect to FIG. 8, if, for example, the voltage level of the power source meets the pre-RRT threshold, then processing may determine that pre-RRT has been met (YES of 1004). In response, the processing circuitry may indicate pre-RRT and initiate a pre-RRT to RRT timer (1006). For example, the processing circuitry may control timer circuitry (e.g., timer circuitry 96) to start a timer (e.g., a countdown from 180 days). The processing circuitry may continue to determine the values of the one or more parameters of the power source (1008).

The processing circuitry may determine that an RRT criterion has been met (YES of 1010). For example, one RRT criterion may include the expiration of the pre-RRT to RRT timer. In an example, an RRT criterion may include the voltage level of the power source reaching (e.g., meeting or exceeding) an RRT backup voltage threshold. Other criteria may be used for determining that the RRT criterion has been met. In an example, if any criterion is met, such as the first criterion in time to be met, then the processing circuitry may determine that the criterion has been met. In response the RRT criterion being met, the processing circuitry may indicate RRT and start an RRT to EOS timer (1012). For example, the processing circuitry may control the timer circuitry to start a timer as described herein. The processing circuitry may continue to determine the values of the one or more parameters of the power source (1014).

The processing circuitry may determine that an EOS criterion has been met (YES of 1016). For example, an EOS criterion may include the expiration of the RRT to EOS timer. In an example, an EOS criterion may include the voltage level of the power source reaching an EOS backup voltage threshold. Other criteria may be used for determining that the EOS criterion has been met. In an example, if any criterion is met, such as the first criterion in time to be met, then the processing circuitry may determine that the criterion has been met. In response to the EOS criterion being met, the processing circuitry may indicate EOS (1018).

Figure 11:
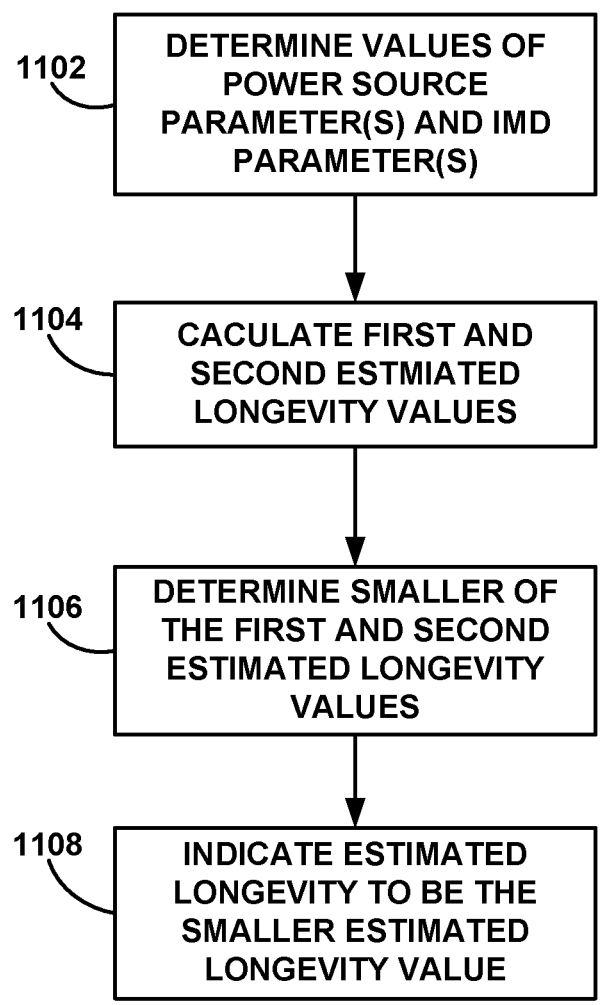
FIG. 11 is a flow diagram illustrating an example technique for indicating an estimated remaining longevity of a power source.

FIG. 11 is a flow diagram illustrating an example technique for indicating an estimated remaining longevity of a power source. An IMD (e.g., IMD 16, such as via processing circuitry 80) may determine values of one or more power source parameters and values of one or more IMD parameters (1102). Such parameters (e.g., the power source parameters and/or the IMD parameters) may be any parameter described herein. The parameters may be instantaneous or measured over time, such as an average or other statistical measure. In some examples, the parameters may be based on a function and determined by processing circuitry. In some examples, parameters may be based on information stored in the memory of the IMD, such as historical or template data relating to the parameter.

In an example, the processing circuitry may calculate a first estimated longevity value and a second estimated longevity value (1104). Referring to FIG. 9, for example, the first estimated longevity value may be the expiration of timer duration 994 and the second estimated longevity value may correspond to the RRT backup 968 threshold voltage.

In an example, the processing circuitry may determine the smaller of the first and second estimated longevity values (1106). For example, the processing circuitry may compare the first and second estimated longevity values to determine the smaller. In an example, if the values are the same (e.g., the same or nearly the same), then the processing circuitry may indicate either, or may indicate the one having a higher certainty estimate, for example.

In an example, the processing circuitry may indicate the estimate remaining longevity of the power source of the IMD to be the smaller estimated longevity value (1108). In the example of FIG. 9, the smaller estimate longevity value was the RRT backup 968 value, therefore that was indicated to be the estimated remaining longevity from the instant time 922.

Various aspects of the techniques may be implemented within one or more processing circuitries, including one or more microprocessors, DSPs, ASICs, FPGAs, or any other equivalent integrated or discrete logic circuitry, as well as any combinations of such components, embodied in external devices, such as physician or patient external devices, electrical stimulators, or other devices. The term "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processing circuitries, such as one or more DSPs, ASICs, FPGAs, general purpose microprocessors, or other equivalent integrated or discrete logic circuitry. Accordingly, the term "processing circuitry,"

as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external device, a combination of an IMD and external device, an integrated circuit (IC) or a set of ICs, and/or discrete electrical circuitry, residing in an IMD and/or external device.

Various aspects of the disclosure have been described. These and other aspects are within the scope of the following claims.

What is claimed is:

1. A method for determining an estimated remaining longevity of a power source of an implantable medical device, the method comprising:
    determining values of one or more parameters of the power source and one or more operational parameters of the implantable medical device;
    calculating, based on at least some of the determined values of the one or more parameters of the power source and the one or more operational parameters of the implantable medical device, a first estimated duration until the one or more parameters of the power source reach a pre-recommended replacement time (pre-RRT) threshold and adding a timer duration to determine a first estimated longevity value;
    calculating, based on the at least some of the determined values of the one or more parameters of the power source and the one or more operational parameters of the implantable medical device, a second estimated duration until the one or more parameters of the power source reach a recommended replacement time (RRT) backup threshold as a second estimated longevity value;
    determining the estimated remaining longevity based on the first and second estimated longevity values; and
    indicating the determined estimated remaining longevity.

2. The method of claim 1, wherein determining the estimated remaining longevity based on the first and second estimated longevity values comprises determining the estimated remaining longevity to be the smaller of the first and second estimated longevity values.

3. The method of claim 2, wherein determining the estimated remaining longevity to be the smaller of the first and second estimated longevity values is determined before the pre-RRT threshold.

4. The method of claim 1, further comprising:
    comparing, during the timer duration, a remaining duration of the timer duration to a duration until the second estimated longevity value; and
    indicating the determined estimated remaining longevity to be the smaller of the remaining duration and the second estimated longevity value.

5. The method of claim 1, wherein the one or more parameters of the power source comprise at least one of an instantaneous battery voltage or an average battery voltage.

6. The method of claim 1, wherein the one or more operational parameters of the implantable medical device comprise at least one of:
    a depth of discharge;
    a stimulation parameter; or
    a bioelectrical sensing parameter.

7. The method of claim 1, wherein the pre-RRT threshold is about 2.625 volts.

8. The method of claim 1, wherein the RRT backup threshold is about 2.600 volts.

9. The method of claim 1, wherein the timer duration is 180 days.

10. A method for indicating a recommended replacement time (RRT) for a power source of an implantable medical device, the method comprising:
    determining values of a parameter of the power source;
    determining, based on the determined values of the parameter of the power source, that the parameter has reached a pre-recommended replacement time (pre-RRT) threshold;
    starting, in response to determining that the parameter has reached the pre-RRT threshold, a pre-RRT to RRT timer;
    indicating the RRT in response to an earlier of the determined values of the parameter of the power source reaching an RRT backup threshold or an expiration of the pre-RRT to RRT timer;
    starting, in response to indicating the RRT, an RRT to end of service (EOS) timer; and
    indicating the EOS in response to an earlier of the determined values of the parameter of the power source reaching an EOS backup threshold or an expiration of the RRT to EOS timer.

11. The method of claim 10, wherein the pre-RRT threshold is about 2.625 volts.

12. The method of claim 10, wherein the RRT backup threshold is about 2.600 volts.

13. The method of claim 10,
    wherein the parameter of the power source comprises a voltage, and
    wherein the determined values of the parameter of the power source define a voltage curve over time, the voltage curve comprising a first plateau and a second plateau, and the RRT backup threshold occurring during a time within the second plateau.

14. The method of claim 10, wherein a duration of the pre-RRT to RRT timer is 180 days.

15. The method of claim 10, wherein a duration of the RRT to EOS timer is 180 days.

16. A medical device system for determining an estimated remaining longevity of a power source, the medical device system comprising:
    an implantable medical device (IMD) that comprises the power source;
    processing circuitry configured to determine values of one or more parameters of the power source and one or more operational parameters of the IMD,
    wherein the processing circuitry is further configured to calculate, based on at least some of the determined values of the one or more parameters of the power source and the one or more operational parameters of the implantable medical device, a first estimated duration until the one or more parameters of the power source reach a pre-recommended replacement time (pre-RRT) threshold and the processing circuitry is further configured to add a timer duration to determine a first estimated longevity value, wherein the processing circuitry is further configured to calculate, based on the at least some of the determined values of the one or more parameters of the power source and the one or more operational parameters of the implantable medical device, a second estimated duration until the one or more parameters of the power source reach a recommended replacement time (RRT) backup threshold as a second estimated longevity value, wherein the processing circuitry is further configured to determine the estimated remaining longevity based on the first and second estimated longevity values, and wherein the processing circuitry is further configured to indicate the determined estimated remaining longevity.

17. The medical device system of claim 16, wherein the processing circuitry is further configured to determine the estimated remaining longevity based on the first and second estimated longevity values by determining the estimated remaining longevity to be the smaller of the first and second estimated longevity values, and wherein the processing circuitry is configured to indicate the smaller of the first and second estimated longevity values as the estimated remaining longevity.

18. The medical device system of claim 17, wherein the processing circuitry is further configured to:

compare, during the timer duration, a remaining duration of the timer duration to a duration until the second estimated longevity value; and indicate the determined estimated longevity of the power source to be the smaller of the remaining duration and the second estimated longevity value.

19. The medical device system of claim 16, wherein the pre-RRT threshold is about 2.625 volts.

20. The medical device system of claim 16, wherein the one or more parameters of the power source comprise a voltage curve of the power source over time, the voltage curve comprising a first plateau and a second plateau, and wherein the RRT backup threshold occurs in the second plateau.

21. A medical device system for indicating a recommended replacement time (RRT) for a power source, the medical device system comprising:

an implantable medical device (IMD) that comprises the power source;

processing circuitry configured to determine values of a parameter of the power source, wherein the processing circuitry is further configured to determine, based on the determined values of the parameter of the power source, that the parameter has reached a pre-recommended replacement time (pre-RRT) threshold, wherein the processing circuitry is further configured to start, by controlling timer circuitry and in response to determining that the parameter has reached the pre-RRT threshold, a pre-RRT to RRT timer, wherein the processing circuitry is further configured to indicate the RRT in response to an earlier of the determined parameter values of the parameter of the power source reaching an RRT backup threshold or an expiration of the pre-RRT to RRT timer, wherein the processing circuitry is further configured to start, by controlling the timer circuitry and in response to indicating the RRT, an RRT to end of service (EOS) timer, and wherein the processing circuitry is further configured to indicate the EOS in response to an earlier of the determined values of the parameter of the power source reaching an EOS backup threshold or an expiration of the RRT to EOS timer.

22. The medical device system of claim 21, wherein the pre-RRT threshold is about 2.625 volts.

23. The medical device system of claim 21, wherein the RRT backup threshold is about 2.600 volts.

24. The medical device system of claim 21, wherein the parameter of the power source comprises a voltage, and wherein the determined values of the parameter of the power source define a voltage curve over time, the voltage curve comprising a first plateau and a second plateau, and the RRT backup threshold occurring during a time within the second plateau.

25. The medical device system of claim 21, wherein a duration of the pre-RRT to RRT timer is 180 days.

26. The medical device system of claim 21, wherein a duration of the RRT to EOS timer is 180 days.

* * * * *